(12) United States Patent
Erbstoeszer et al.

(10) Patent No.: US 8,406,895 B2
(45) Date of Patent: Mar. 26, 2013

(54) IMPLANTABLE ELECTRICAL LEAD INCLUDING A COOLING ASSEMBLY TO DISSIPATE MRI INDUCED ELECTRODE HEAT

(75) Inventors: Blair Erbstoeszer, Kirkland, WA (US); Brendan E. Koop, Coon Rapids, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 109 days.

(21) Appl. No.: 12/907,657

(22) Filed: Oct. 19, 2010

(65) Prior Publication Data

US 2011/0160805 A1   Jun. 30, 2011

Related U.S. Application Data

(60) Provisional application No. 61/291,154, filed on Dec. 30, 2009.

(51) Int. Cl.
*A61N 1/05*   (2006.01)

(52) U.S. Cl. .............................. 607/115; 607/36; 607/63

(58) Field of Classification Search .................... 607/63, 607/116; 600/373, 377
See application file for complete search history.

(56) References Cited

U.S. PATENT DOCUMENTS

| | | | |
|---|---|---|---|
| 4,437,474 A | 3/1984 | Peers-Trevarton |
| 5,003,975 A | 4/1991 | Hafelfinger et al. |
| 5,201,865 A | 4/1993 | Kuehn |
| 5,370,666 A | 12/1994 | Lindberg et al. |
| 5,476,485 A | 12/1995 | Weinberg et al. |
| 5,534,018 A | 7/1996 | Wahlstrand et al. |
| 5,549,646 A | 8/1996 | Katz et al. |
| 5,727,552 A | 3/1998 | Ryan |
| 5,727,553 A | 3/1998 | Saad |
| 5,755,742 A | 5/1998 | Schuelke et al. |
| 5,766,227 A | 6/1998 | Nappholz et al. |
| 5,800,496 A | 9/1998 | Swoyer et al. |
| 5,817,136 A | 10/1998 | Nappholz et al. |
| 5,891,179 A | 4/1999 | Er et al. |
| 6,016,447 A | 1/2000 | Juran et al. |
| 6,101,417 A | 8/2000 | Vogel et al. |
| 6,192,280 B1 | 2/2001 | Sommer et al. |
| 6,317,633 B1 | 11/2001 | Jorgenson et al. |
| 6,360,129 B1 | 3/2002 | Ley et al. |
| 6,721,600 B2 | 4/2004 | Jorgenson et al. |
| 6,906,256 B1 | 6/2005 | Wang |
| 6,949,929 B2 | 9/2005 | Gray et al. |
| 6,999,818 B2 | 2/2006 | Stevenson et al. |
| 7,013,180 B2 | 3/2006 | Dublin et al. |

(Continued)

FOREIGN PATENT DOCUMENTS

EP   1852810 B1   11/2007
WO   W02010078552 A1   7/2010

OTHER PUBLICATIONS

International Search Report and Written Opinion issued in PCT/US2010/053223, mailed Dec. 27, 2010, 12 pages.

(Continued)

*Primary Examiner* — Carl H Layno
*Assistant Examiner* — Allen Porter, Jr.
(74) *Attorney, Agent, or Firm* — Faegre Baker Daniels LLP

(57) ABSTRACT

An implantable medical device lead includes an insulative lead body, an outer conductive coil extending through the lead body, and an inner conductive coil extending coaxially with the outer conductive coil. The outer conductive coil is coupled to a proximal electrode at a distal end of the outer conductive coil, and the inner conductive coil is coupled to a distal electrode at a distal end of the inner conductive coil. A cooling assembly is thermally coupled to the distal electrode to dissipate heat generated at the distal electrode during exposure to magnetic resonance imaging (MRI) fields.

17 Claims, 4 Drawing Sheets

U.S. PATENT DOCUMENTS

| | | |
|---|---|---|
| 7,047,075 B2 | 5/2006 | Stubbs |
| 7,047,083 B2 | 5/2006 | Gunderson et al. |
| 7,050,855 B2 | 5/2006 | Zeijlemaker et al. |
| 7,113,827 B2 | 9/2006 | Silvestri et al. |
| 7,123,013 B2 | 10/2006 | Gray |
| 7,127,294 B1 | 10/2006 | Wang et al. |
| 7,135,978 B2 | 11/2006 | Gisselberg et al. |
| 7,138,582 B2 | 11/2006 | Lessar et al. |
| 7,174,219 B2 | 2/2007 | Wahlstrand et al. |
| 7,174,220 B1 | 2/2007 | Chitre et al. |
| 7,239,916 B2 | 7/2007 | Thompson et al. |
| 7,289,851 B2 | 10/2007 | Gunderson et al. |
| 7,369,898 B1 | 5/2008 | Kroll et al. |
| 7,388,378 B2 | 6/2008 | Gray et al. |
| 7,535,363 B2 | 5/2009 | Gisselberg et al. |
| 7,630,761 B2 | 12/2009 | Salo et al. |
| 7,953,499 B2 | 5/2011 | Knapp et al. |
| 8,145,324 B1 | 3/2012 | Stevenson et al. |
| 2003/0028231 A1 | 2/2003 | Partridge et al. |
| 2003/0083726 A1 | 5/2003 | Zeijlemaker et al. |
| 2003/0093136 A1 | 5/2003 | Osypka et al. |
| 2003/0140931 A1 | 7/2003 | Zeijlemaker et al. |
| 2003/0144705 A1 | 7/2003 | Funke |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0204217 A1 | 10/2003 | Greatbatch |
| 2004/0064161 A1 | 4/2004 | Gunderson et al. |
| 2004/0172117 A1 | 9/2004 | Hill et al. |
| 2005/0113676 A1 | 5/2005 | Weiner et al. |
| 2005/0113873 A1 | 5/2005 | Weiner et al. |
| 2005/0113876 A1 | 5/2005 | Weiner et al. |
| 2005/0197677 A1 | 9/2005 | Stevenson |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2005/0267556 A1 | 12/2005 | Shuros et al. |
| 2006/0030774 A1 | 2/2006 | Gray et al. |
| 2006/0041294 A1 | 2/2006 | Gray |
| 2006/0041296 A1 | 2/2006 | Bauer et al. |
| 2006/0118758 A1 | 6/2006 | Wang et al. |
| 2006/0247747 A1 | 11/2006 | Olsen et al. |
| 2006/0247748 A1 | 11/2006 | Wahlstrand et al. |
| 2006/0252314 A1 | 11/2006 | Atalar et al. |
| 2006/0271138 A1 | 11/2006 | MacDonald |
| 2007/0010702 A1 | 1/2007 | Wang et al. |
| 2007/0027532 A1 | 2/2007 | Wang et al. |
| 2007/0179577 A1 | 8/2007 | Marshall et al. |
| 2007/0179582 A1 | 8/2007 | Marshall et al. |
| 2007/0191914 A1 | 8/2007 | Stessman |
| 2008/0033497 A1 | 2/2008 | Bulkes et al. |
| 2008/0051854 A1 | 2/2008 | Bulkes et al. |
| 2008/0057784 A1 | 3/2008 | Zarembo et al. |
| 2008/0132985 A1 | 6/2008 | Wedan et al. |
| 2008/0154348 A1 | 6/2008 | Atalar et al. |
| 2008/0208290 A1 | 8/2008 | Phillips et al. |
| 2009/0005825 A1 | 1/2009 | MacDonald |
| 2009/0024180 A1 | 1/2009 | Kisker et al. |
| 2009/0024197 A1 | 1/2009 | Jensen |
| 2009/0149920 A1 | 6/2009 | Li et al. |
| 2009/0149933 A1 | 6/2009 | Ameri |
| 2009/0204171 A1 | 8/2009 | Ameri |
| 2009/0210022 A1 | 8/2009 | Powers |
| 2010/0103215 A1 | 4/2010 | Iriguchi |
| 2010/0106215 A1 | 4/2010 | Stubbs et al. |
| 2010/0125320 A1 | 5/2010 | Polkinghorne et al. |
| 2011/0060394 A1 | 3/2011 | Poore |
| 2011/0087302 A1 | 4/2011 | Ameri |
| 2011/0160816 A1 | 6/2011 | Stubbs et al. |
| 2012/0143273 A1 | 6/2012 | Stubbs et al. |

OTHER PUBLICATIONS

Basso, Christophe, "SPICE Model Simulates Spark-Gap Arrestor", Electronics Design, Strategy, and News (EDN), Jul. 3, 1997, 4 pages.

File History for U.S. Appl. No. 11/015,807, filed Dec. 17, 2004.

International Search Report and Written Opinion issued in PCT/US2009/056843, mailed Dec. 29, 2009, 13 pages.

International Search Report and Written Opinion issued in PCT/US2010/048620, mailed Apr. 5, 2011, 10 pagaes.

Partial International Search Report issued in PCT/US2011/052541, mailed Dec. 6, 2011, 4 pages.

Avalanche Breakdown, Wikipedia Article, captured Apr. 6, 2010, [http://en.wikipedia.org/wiki/Avalanche_breakdown].

Static Spark Gap Analysis, captured Dec. 24, 2002, [http://www.richieburnett.co.uk/static.html].

IMPLANTABLE ELECTRICAL LEAD INCLUDING A COOLING ASSEMBLY TO DISSIPATE MRI INDUCED ELECTRODE HEAT

CROSS-REFERENCE TO RELATED APPLICATION

This application claims priority to Provisional Application No. 61/291,154, filed Dec. 30, 2009, which is herein incorporated by reference in its entirety.

TECHNICAL FIELD

The present invention relates to implantable medical devices. More particularly, the present invention relates to implantable medical device leads including integrated cooling assemblies.

BACKGROUND

Magnetic resonance imaging (MRI) is a non-invasive imaging procedure that utilizes nuclear magnetic resonance techniques to render images within a patient's body. Typically, MRI systems employ the use of a magnetic coil having a magnetic field strength of between about 0.2 to 3 Teslas. During the procedure, the body tissue is briefly exposed to RF pulses of electromagnetic energy in a plane perpendicular to the magnetic field. The resultant electromagnetic energy from these pulses can be used to image the body tissue by measuring the relaxation properties of the excited atomic nuclei in the tissue.

During imaging, the electromagnetic radiation produced by the MRI system may be picked up by implantable device leads used in implantable medical devices such as pacemakers or cardiac defibrillators. This energy may be transferred through the lead to the electrode in contact with the tissue, which may lead to elevated temperatures at the point of contact. The degree of tissue heating is typically related to factors such as the length of the lead, the conductivity or impedance of the lead, and the surface area of the lead electrodes. Exposure to a magnetic field may also induce an undesired voltage on the lead.

SUMMARY

Discussed herein are various components for implantable medical electrical leads including a cooling assembly that dissipates heat generated in the lead electrode(s) during exposure to magnetic resonance imaging (MRI) fields, as well as medical devices including such implantable medical electrical leads.

In Example 1, an implantable medical device lead includes an insulative lead body, an outer conductive coil extending through the lead body, and an inner conductive coil extending coaxially with the outer conductive coil. The outer conductive coil is coupled to a proximal electrode at a distal end of the outer conductive coil, and the inner conductive coil is coupled to a distal electrode at a distal end of the inner conductive coil. A cooling assembly is thermally coupled to the distal electrode to dissipate heat generated at the distal electrode during exposure to magnetic resonance imaging (MRI) fields.

In Example 2, the implantable medical device lead according to Example 1, wherein the cooling assembly comprises one or more thermoelectric elements encased in a thermally conductive biocompatible material.

In Example 3, the implantable medical device lead according to either Example 1 or 2, wherein the one or more thermoelectric elements are configured to electrically couple to an energy storage device that drives the one or more thermoelectric elements to pull heat from the distal electrode.

In Example 4, the implantable medical device lead according to any of Examples 1-3, wherein energy generated during exposure of the implantable medical device lead to MRI fields is stored in the energy storage device, and wherein the one or more thermoelectric elements are driven at least in part by the energy stored in the energy storage device during exposure of the implantable medical device lead to MRI fields.

In Example 5, the implantable medical device lead according to any of Examples 1-4, wherein the one or more thermoelectric elements are configured to electrically couple to an energy storage device that stores energy generated by the one or more thermoelectric elements when dissipating heat from the distal electrode.

In Example 6, the implantable medical device lead according to any of Examples 1-5, wherein the one or more thermoelectric elements are configured to electrically couple to a heat sink that dissipates energy generated by the one or more thermoelectric elements when dissipating heat from the distal electrode.

In Example 7, the implantable medical device lead according to any of Examples 1-6, wherein the one or more thermoelectric elements are arranged circumferentially around a distal end of the implantable medical device lead.

In Example 8, the implantable medical device lead according to any of Examples 1-7 wherein the one or more thermoelectric elements are arranged at a distal tip of the implantable medical device lead, and wherein the one or more thermoelectric elements include a central metal element and a metal ring separated by a ring of heat transfer junction material.

In Example 9, a medical device includes a pulse generator and a lead including a lead body. An outer conductive coil extends through the lead body, and an inner conductive coil extends coaxially with the outer conductive coil. The outer conductive coil is coupled to a proximal electrode at a distal end of the outer conductive coil, and the inner conductive coil is coupled to a distal electrode at a distal end of the inner conductive coil. A cooling assembly is thermally coupled to the distal electrode and electrically coupled to the pulse generator to dissipate heat generated at the distal electrode during exposure to magnetic resonance imaging (MRI) fields.

In Example 10, the medical device according to Example 9, wherein the cooling assembly comprises one or more thermoelectric elements encased in a thermally conductive biocompatible material.

In Example 11, the medical device according to either Example 9 or 10, wherein the pulse generator includes an energy storage device, and wherein the one or more thermoelectric elements are electrically coupled to the energy storage device, the energy storage device driving the one or more thermoelectric elements to pull heat from the distal electrode.

In Example 12, the medical device according to any of Examples 9-11, wherein energy generated during exposure of the implantable medical device lead to MRI fields is stored in the energy storage device, and wherein the one or more thermoelectric elements are driven at least in part by the energy stored in the energy storage device during exposure of the implantable medical device lead to MRI fields.

In Example 13, the medical device according to any of Examples 9-12, wherein the pulse generator includes an energy storage device, and wherein the one or more thermoelectric elements are electrically coupled to the energy storage device to store energy generated by the one or more thermoelectric elements when dissipating heat from the distal electrode.

In Example 14, the medical device according to any of Examples 9-13, wherein the pulse generator includes a heat sink, and wherein the one or more thermoelectric elements are electrically coupled to the heat sink to dissipate energy generated by the one or more thermoelectric elements when dissipating heat from the distal electrode.

In Example 15, the medical device according to any of Examples 9-14, wherein the one or more thermoelectric elements are arranged circumferentially around a distal end of the implantable medical device lead.

In Example 16, the medical device according to any of Examples 9-15, wherein the one or more thermoelectric elements are arranged at a distal tip of the implantable medical device lead, and wherein the one or more thermoelectric elements include a central metal element and a metal ring element separated by a ring of heat transfer junction material.

In Example 17, a medical device includes a pulse generator including an energy storage device and a lead including an insulative lead body and an inner conductor assembly extending coaxially with the outer conductive coil. An inner conductor assembly extends coaxially with the outer conductive coil and includes at least first, second, and third filars. The first filar is coupled to the pulse generator at a proximal end of the first filar and to a distal electrode at a distal end of the first filar. A cooling assembly is thermally coupled to the distal electrode to dissipate heat generated at the distal electrode during exposure to magnetic resonance imaging (MRI) fields. The cooling assembly is electrically coupled to the energy storage device via the second and third filars.

In Example 18, the medical device according to Example 17, wherein the first, second, and third filars of the inner conductor assembly are co-radial.

In Example 19, the medical device according to either Example 17 or 18, wherein the energy storage device drives the cooling assembly to pull heat from the distal electrode.

In Example 20, the medical device according to any of Examples 17-19, wherein the cooling assembly generates energy when dissipating heat from the distal electrode, and wherein the energy generated by the cooling assembly is stored in the energy storage device.

In Example 21, the medical device according to any of Examples 17-20, wherein the cooling assembly comprises one or more thermoelectric elements encased in a thermally conductive biocompatible material.

In Example 22, the medical device according to any of Examples 17-21, wherein the one or more thermoelectric elements are arranged circumferentially around a distal end of the implantable medical device lead.

In Example 23, the medical device according to any of Examples 17-22, wherein the one or more thermoelectric elements are arranged at a distal tip of the implantable medical device lead, and wherein the one or more thermoelectric elements include a central metal element and a metal ring element separated by a ring of heat transfer junction material.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
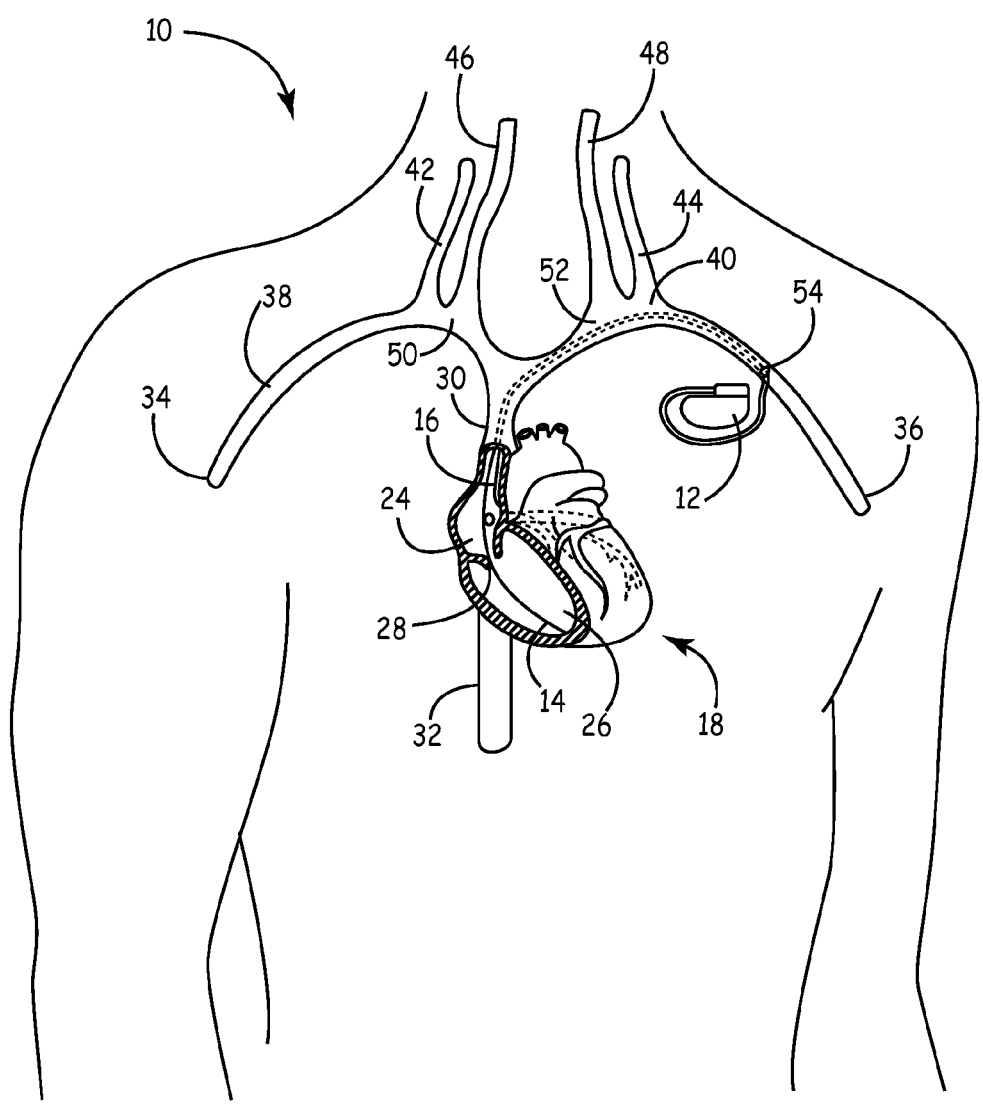
FIG. 1 is a schematic view of a cardiac rhythm management (CRM) system including a pulse generator and a lead implanted in a patient's heart according to an embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of a cardiac rhythm management (CRM) system 10 according to an embodiment of the present invention. As shown in FIG. 1, the CRM system 10 includes a pulse generator 12 coupled to a plurality of leads 14, 16 deployed in a patient's heart 18. As further shown in FIG. 1, the heart 18 includes a right atrium 24 and a right ventricle 26 separated by a tricuspid valve 28. During normal operation of the heart 18, deoxygenated blood is fed into the right atrium 24 through the superior vena cava 30 and the inferior vena cava 32. The major veins supplying blood to the superior vena cava 30 include the right and left axillary veins 34 and 36, which flow into the right and left subclavian veins 38 and 40. The right and left external jugular 42 and 44, along with the right and left internal jugular 46 and 48, join the right and left subclavian veins 38 and 40 to form the right and left brachiocephalic veins 50 and 52, which in turn combine to flow into the superior vena cava 30.

The leads 14, 16 operate to convey electrical signals and stimuli between the heart 18 and the pulse generator 12. In the illustrated embodiment, the lead 14 is implanted in the right ventricle 26, and the lead 16 is implanted in the right atrium 24. In other embodiments, the CRM system 10 may include additional leads, e.g., a lead extending into a coronary vein for stimulating the left ventricle in a bi-ventricular pacing or cardiac resynchronization therapy system. As shown, the leads 14, 16 enter the vascular system through a vascular entry site 54 formed in the wall of the left subclavian vein 40, extend through the left brachiocephalic vein 52 and the superior vena cava 30, and are implanted in the right ventricle 26 and right atrium 24, respectively. In other embodiments of the present invention, the leads 14, 16 may enter the vascular system through the right subclavian vein 38, the left axillary vein 36, the left external jugular 44, the left internal jugular 48, or the left brachiocephalic vein 52.

The pulse generator 12 is typically implanted subcutaneously within an implantation location or pocket in the patient's chest or abdomen. The pulse generator 12 may be any implantable medical device known in the art or later developed, for delivering an electrical therapeutic stimulus to the patient. In various embodiments, the pulse generator 12 is a pacemaker, an implantable cardiac defibrillator, and/or includes both pacing and defibrillation capabilities. The portion of the leads 14, 16 extending from the pulse generator 12 to the vascular entry site 54 are also located subcutaneously or submuscularly. The leads 14, 16 are each connected to the pulse generator 12 via proximal connectors. Any excess lead length, i.e., length beyond that needed to reach from the pulse generator 12 location to the desired intracardiac implantation site, is generally coiled up in the subcutaneous pocket near the pulse generator 12.

The electrical signals and stimuli conveyed by the pulse generator 12 are carried to electrodes at the distal ends of leads 14, 16 by one or more conductors extending through the leads 14, 16. The one or more conductors are each electrically coupled to a connector suitable for interfacing with the pulse generator 12 at the proximal end of the leads 14, 16 and to one or more electrodes at the distal end. In an MRI environment, the electromagnetic radiation produced by the MRI system may be picked up by conductors of the leads 14, 16. This energy may be transferred through the leads 14, 16 to the electrode in contact with the tissue, which may lead to elevated temperatures at the point of contact. The present invention relates to a bipolar lead having an inner conductive assembly including a plurality of series connected current suppression modules that reduces heating due to MRI induced energy. The bipolar lead also includes an outer conductive coil configured to minimize the effect on the energy picked up by the inner conductive assembly.

Figure 2:
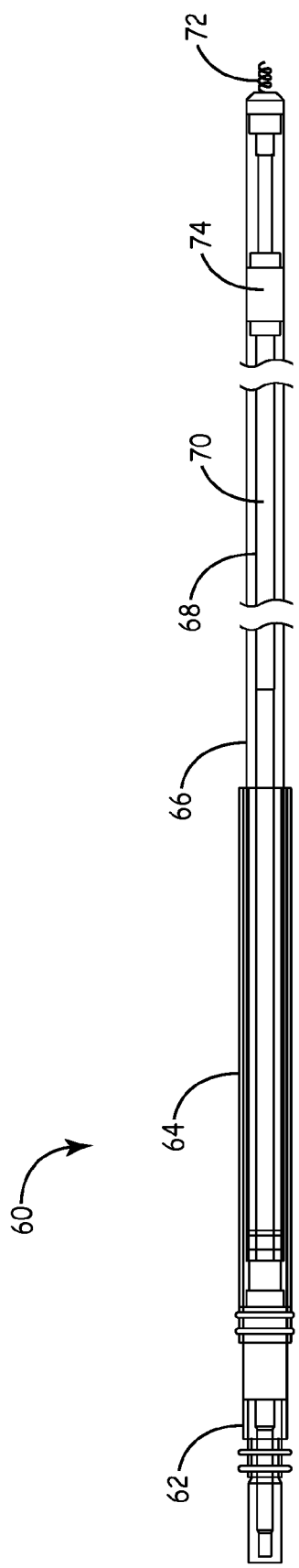
FIG. 2 is a side view of a lead suitable for use with the CRM system shown in FIG. 1.

FIG. 2 is a side view of a lead 60 that may be suitable for use with the CRM system 10 shown in FIG. 1. That is, the leads 14 and/or 16 shown in FIG. 1 may be configured similarly to the lead 60. The lead 60 includes a proximal connector 62, an insulative lead body 64, an outer conductive coil 66, an insulative layer 68, and an inner conductive assembly 70. In some embodiments, the inner conductor assembly 70 is a co-radial or coaxial assembly of coils that extends from a connector 62 at the proximal end of the lead 60 to one or more electrodes 72 and an active cooling device at the distal end of the lead 60. The outer conductive coil 66 extends coaxially with the inner conductor assembly 70 and is electrically isolated from the inner conductor assembly 70 by the insulative layer 68. The outer conductive coil 66 is connected to the connector 62 at the proximal end of the lead 60 and to one or more electrodes 74 at the distal end of the lead 14. The insulative lead body 64 surrounds the outer conductive coil 66 and supports the one or more electrodes 72, 74 electrically coupled to a distal ends of the inner conductor assembly 70 and outer conductive coil 66, respectively. The connector 62 is configured to couple to the pulse generator 12 (FIG. 1) and electrically connects the electrodes 72, 74 to the pulse generator 12 via the inner conductor assembly 70 and outer conductive coil 66, respectively. The electrodes 72, 74 are merely illustrative, and may be configured for use in pacing, sensing, heart failure, and/or shock therapy applications. In addition, while active fixation electrode 72 is shown, the electrode 72 may alternatively be configured for passive fixation of the lead 60 to tissue of the heart 18, or without a fixation mechanism.

Figure 3:
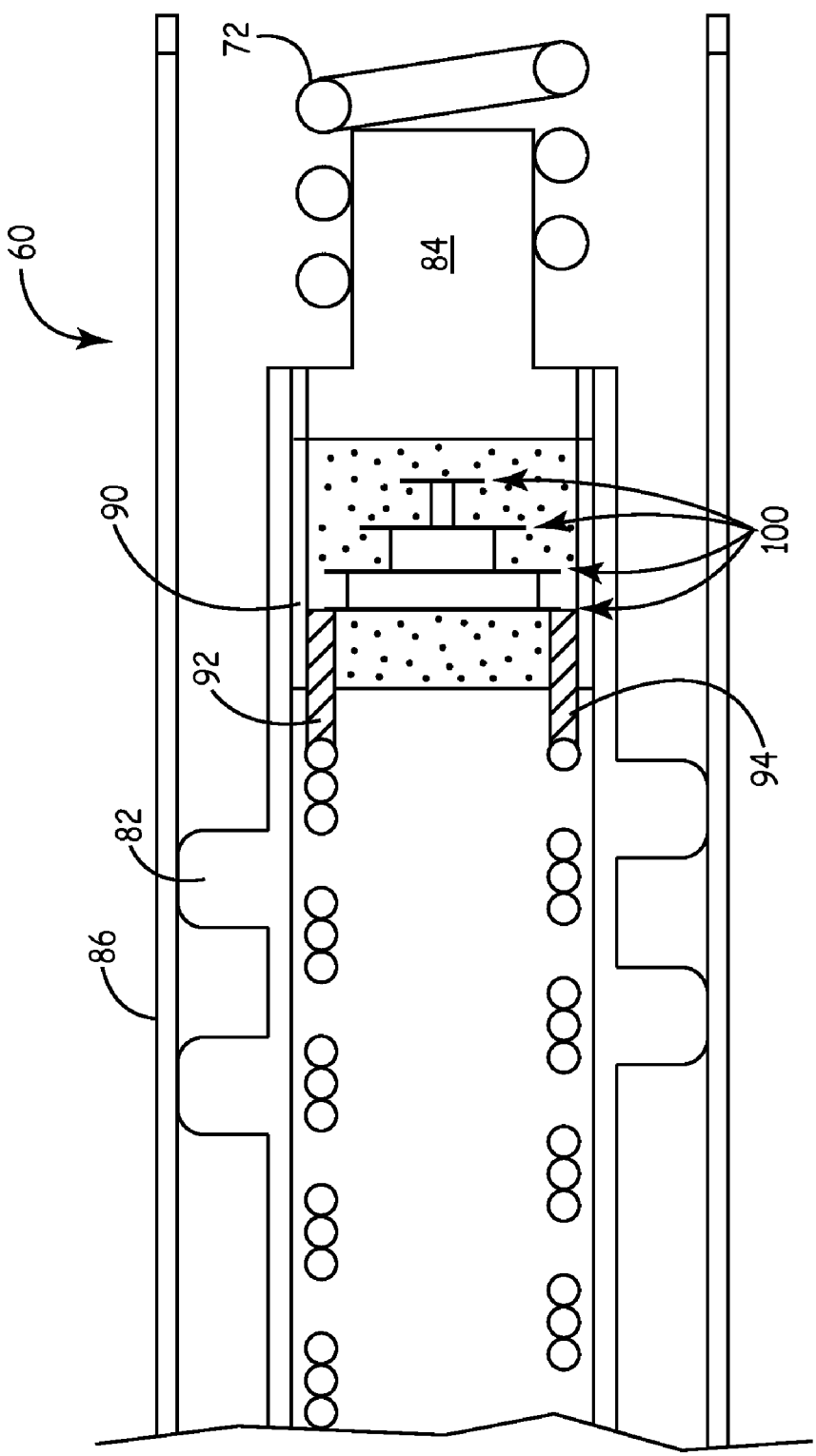
FIG. 3 is a cross-sectional view of a distal end of an embodiment of a lead including a cooling assembly arranged to dissipate MRI-induced heat from the distal electrode.

FIG. 3 is a cross-sectional view of a distal end of an embodiment of the lead 60. The portion of the lead 60 shown includes the inner conductor assembly 70, the distal electrode 72, and a cooling assembly 80, a proximal base portion 82 and a distal base portion 84 contained in a cathode housing 86. For ease of illustration, the insulative lead body 64, outer conductive coil 66, insulative layer 68, and proximal electrode 74 are not shown in FIG. 3. In some embodiments, the proximal base portion 82 and distal base portion 84 are configured to rotate with respect to the cathode housing 86 to extend and retract the distal electrode 72. For example, the fixation mechanism may be configured as is shown and described in U.S. Prov. Patent App. Ser. No. 61/221,704, entitled "Extendable/Retractable Lead with Improved Distal Seal," which is hereby incorporated by reference in its entirety. In alternative embodiments, the distal electrode 72 may have other configurations, such as a fixed helix or a tip electrode with or without passive fixation.

The inner conductor assembly 70 includes first filar 90, second filar 92, and third filar 94. The first filar 90 is connected to the distal electrode 72, and the second filar 92 and third filar 94 are connected to the cooling assembly 80. In the embodiment shown, the filars 90, 92, 94 are co-radial. In alternative embodiments, some or all of the filars 90, 92, 94 are coaxial and/or the inner conductor assembly 70 includes more or fewer filars. The filars 90, 92, 94 may also be insulated filars. Furthermore, while adjacent turns of the filars 90, 92, 94 are shown spaced apart for illustrative purposes, in actual implementation adjacent turns of the filars 90, 92, 94 may be closely wound.

The distal electrode 72 is thermally coupled to the cooling assembly 80 via the proximal base portion 82 and distal base portion 84. In some embodiments, at least one of the proximal base portion 82 and distal electrode base 84 is comprised of a biocompatible metal for thermal conductivity. In other embodiments, the proximal base portion 82 may be made of a non-metal material, such as, for example, Teflon, Nylon, polymers, polytetrafluoroethylene (PTFE), ethylene tetrafluoroethylene (ETFE). The first filar 90 extends past the cooling assembly 80 and connects to the distal electrode base electrically couples the distal electrode 72 to the connector 62 via the first filar 90 of the inner conductor assembly 70.

The cooling assembly 80 comprises one or more thermoelectric elements 100 encased or surrounded by a thermally conductive insulating material. In some embodiments, the thermoelectric elements 100 comprise one or more Peltier elements. In the embodiment shown, the cooling assembly 80 includes four stacked thermoelectric elements 100. Each of the thermoelectric elements 100 comprises coupled N- and P-type semiconductor materials connected in series to form thermoelectric arrays. The thermoelectric arrays may be mounted on ceramic substrates to mechanically hole the arrays together. The different types of material in the thermoelectric elements 100 are arranged such that the charge carriers (i.e., electrons for the N-type semiconductor materials and electron holes for the P-type semiconductor materials) and heat flow in the same direction through the thermoelectric elements 100. In some embodiments, the N- and P-type semiconductor materials comprise N- and P-type bismuth telluride ($Bi_2Te_3$), respectively. The thermoelectric elements 100 are arranged in the cooling assembly 80 such the charge carriers and heat flow away from the distal electrode 72. In some embodiments, the stack of thermoelectric elements 100 is such that the Peltier element 100 closest to the distal electrode 72 is comprised of a smaller array of semiconductor materials than the thermoelectric elements 100 further from the distal electrode 72. This is because each Peltier element 100 further from the distal electrode 72 not only dissipates heat from its own internal power dissipation and from the distal electrode 72, but also removes heat from the thermoelectric elements 100 closer to the distal electrode 72.

The thermoelectric elements 100 are electrically coupled to the connector 62 via the second filar 92 and third filar 94 of the inner conductor assembly 70. The connector 62 electrically connects the filars 92, 94 to components of the pulse generator 12. In some embodiments, when the connector 62 is coupled to the pulse generator 12, the thermoelectric elements 100 are electrically coupled to an energy storage device in the pulse generator 12 via the filars 92, 94. For example, the energy storage device may be a rechargeable battery or capacitor in the pulse generator.

In one aspect, the energy storage device in the pulse generator 12 is employed to develop a voltage differential across the cooling assembly 80 to actively cool the distal electrode 72 by drawing heat from the distal side of the cooling assembly 80 to the proximal side of the cooling assembly 80. The cooling assembly 80 may be thermally coupled to a heat sink within the lead (not shown) to dissipate heat drawn to the proximal side of the cooling assembly 80. In some embodiments, the energy used to power the cooling assembly 80 may be drawn from the battery in the pulse generator 12. In other embodiments, the energy generated on the inner conductor assembly 70 in the presence of the MRI fields (which may be stored in an energy storage device in the pulse generator 12) may be used to power the cooling assembly 80.

In some embodiments, the pulse generator 12 is configured to drive the cooling assembly 80 when in the presence of MRI fields. For example, the pulse generator 12 may be configured with an MRI mode that is an operational mode of the pulse generator 12 that is a safe operational mode in the presence of electromagnetic interference (EMI). When the pulse generator 12 is switched to the MRI mode (e.g., based on a signal received from an external device or upon detection of MRI fields), the pulse generator 12 may begin driving the cooling assembly 80. In other embodiments, the pulse generator 12 may include MRI field detection circuitry that initiates powering of the cooling assembly 80 upon detection of MRI fields. In further aspects, the lead 60 may include a temperature sensor at or near the distal electrode 72 operatively connected the pulse generator 12, which initiates powering of the cooling assembly 80 when the distal electrode 72 heats to a threshold temperature.

In another aspect, the cooling assembly 80 operates to passively cool the distal electrode 72 by converting heat energy from the distal electrode 72 to electrical energy for dissipation. The electrical energy generated by the thermoelectric elements 100 is carried by the filars 92, 94 to the pulse generator 12. In some embodiments, the electrical energy delivered to the pulse generator 12 by the filars 92, 94 is stored in an energy storage device (e.g., battery or capacitor). In other embodiments, the electrical energy from the filars 92, 94 is dissipated in a heat sink disposed in the pulse generator 12.

Figure 4:
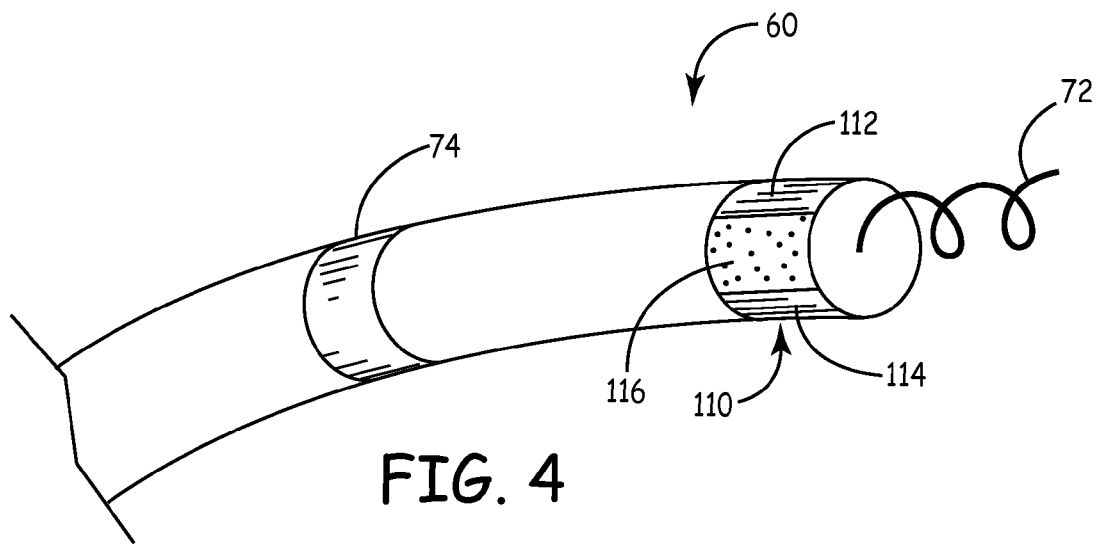
FIG. 4 is a perspective view of a distal end of an embodiment of a lead including a cooling assembly disposed circumferentially around the distal end of the lead.

The configuration and location of the cooling assembly 80 is merely exemplary, and cooling assemblies having other configurations are also possible. For example, FIG. 4 is a perspective view of another embodiment of the lead 60 including a cooling assembly 110 located near a distal end of the lead 60. The cooling assembly 110 is thermally coupled to the distal electrode 74. While the distal electrode 74 is illustrated as a fixed helix, other configurations for the distal electrode 74 as discussed above are also possible. The cooling assembly 110 is disposed circumferentially around a distal end of the lead 60 and includes a first metal 112 and a second metal 114 separated by a heat transfer junction 116. In some embodiments, the first metal 112 and second metal 114 are dissimilar metals that exhibit the Peltier effect. The first metal 112 may be electrically coupled to the second filar 92 and the second metal 114 may be electrically coupled to the third filar 94 to connect the cooling assembly 110 to the pulse generator 12. In this arrangement, the cooling assembly 110 may be operated as an active or passive cooling device similar to cooling assembly 80 as described above.

Figure 5:
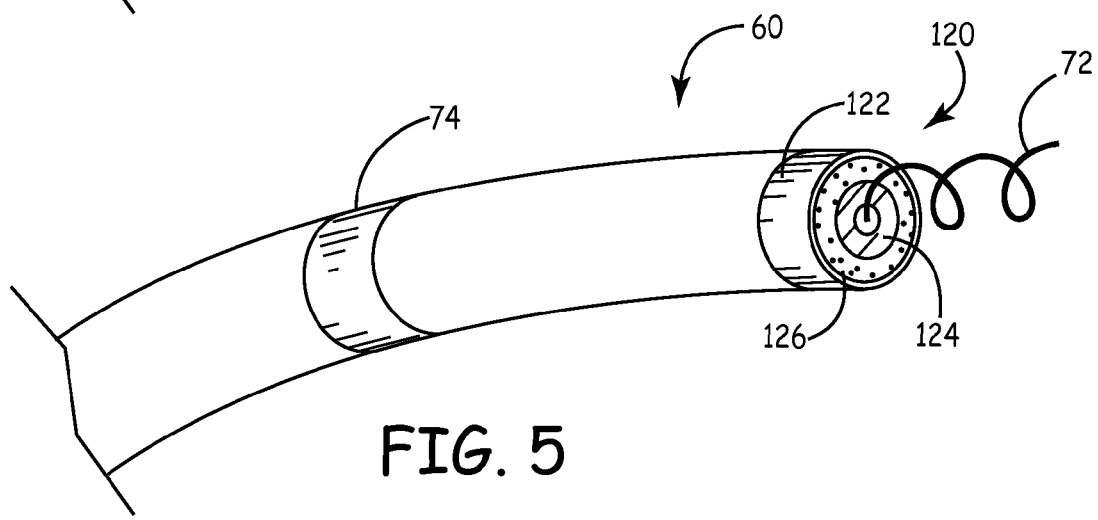
FIG. 5 is a perspective view of a distal end of an embodiment of a lead including a fixation helix and a cooling assembly disposed at the distal end of the lead.

FIG. 5 is a perspective view of another embodiment of the lead 60 including a cooling assembly 120 located at the distal tip of the lead 60. The cooling assembly 120 is thermally coupled to the distal electrode 74. The cooling assembly 120 includes a first metal 122 and a second metal 124 separated by a heat transfer junction 126. The first metal 122 is disposed circumferentially around the distal end of the lead 60, and the second metal 124 is configured as a ring-like element at the distal tip of the lead 60. The heat transfer junction 126 is a ring-like element disposed between the first metal 124 and the second metal 126. In some embodiments, the first metal 122 and second metal 124 are dissimilar metals that exhibit the Peltier effect. The first metal 122 may be electrically coupled to the second filar 92 and the second metal 124 may be electrically coupled to the third filar 94 to connect the cooling assembly 120 to the pulse generator 12. In this arrangement, the cooling assembly 120 may be operated as an active or passive cooling device similar to cooling assembly 80 as described above.

Figure 6:
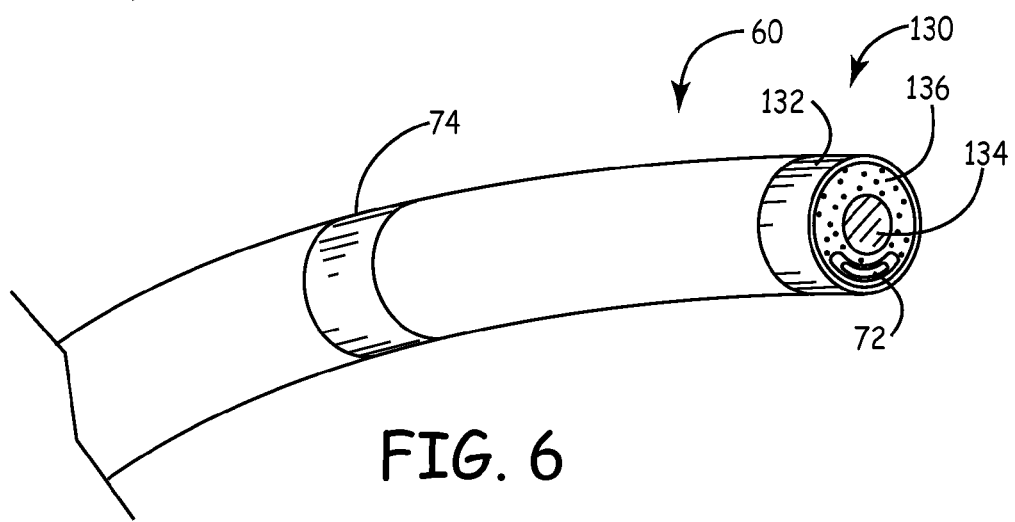
FIG. 6 is a perspective view of a distal end of an embodiment of a lead including an extendable/retractable fixation helix and a cooling assembly disposed at the distal end of the lead.

While the distal electrode 74 in FIG. 5 is illustrated as a fixed helix, other electrode configurations are possible. For example, FIG. 6 illustrates a cooling assembly 130 located at the distal tip of the lead 60 including an extendable/retractable distal electrode 74. The distal electrode 74 is shown retracted into the body of the lead 60 in FIG. 6. The cooling assembly 130 is thermally coupled to the distal electrode 74. The cooling assembly 130 includes a first metal 132 and a second metal 134 separated by a heat transfer junction 136. The first metal 132 is disposed circumferentially around the distal end of the lead 60, and the second metal 134 is configured as a disc-like element at the distal tip of the lead 60. The heat transfer junction 136 is a ring-like element disposed between the first metal 134 and the second metal 136. In some embodiments, the first metal 132 and second metal 134 are dissimilar metals that exhibit the Peltier effect. The first metal 132 may be electrically coupled to the second filar 92 and the second metal 134 may be electrically coupled to the third filar 94 to connect the cooling assembly 130 to the pulse generator 12. In this arrangement, the cooling assembly 130 may be operated as an active or passive cooling device similar to cooling assembly 80 as described above.

In summary, embodiments of the present invention relate to an implantable medical device lead including an insulative lead body, an outer conductive coil extending through the lead body, and an inner conductive coil extending coaxially with the outer conductive coil. The outer conductive coil is coupled to a proximal electrode at a distal end of the outer conductive coil, and the inner conductive coil is coupled to a distal electrode at a distal end of the inner conductive coil. A cooling assembly is thermally coupled to the distal electrode to dissipate heat generated at the distal electrode during exposure to magnetic resonance imaging (MRI) fields.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof. For example, while the cooling assemblies described relate to dissipating heat at the distal electrode of the leads, cooling assemblies can alternatively or additionally be configured to dissipate heat from other electrodes and components of the leads.

We claim:

1. An implantable medical device lead comprising:
an insulative lead body;
an outer conductive coil extending through the lead body, the outer conductive coil coupled to a proximal electrode at a distal end of the outer conductive coil;
an inner conductive coil extending coaxially with the outer conductive coil and coupled to a distal electrode at a distal end of the inner conductive coil; and
a cooling assembly thermally coupled to the distal electrode to dissipate heat generated at the distal electrode during exposure to magnetic resonance imaging (MRI) fields, wherein the cooling assembly comprises one or more thermoelectric elements encased in a thermally conductive biocompatible material, and wherein the one or more thermoelectric elements are configured to electrically couple to an energy storage device that stores energy generated by the one or more thermoelectric elements when dissipating heat from the distal electrode.

2. The implantable medical device lead of claim 1, wherein the one or more thermoelectric elements are configured to electrically couple to an energy storage device that drives the one or more thermoelectric elements to pull heat from the distal electrode.

3. The implantable medical device lead of claim 2, wherein energy generated during exposure of the implantable medical device lead to MRI fields is stored in the energy storage device, and wherein the one or more thermoelectric elements are driven at least in part by the energy stored in the energy storage device during exposure of the implantable medical device lead to MRI fields.

4. The implantable medical device lead of claim 1, wherein the one or more thermoelectric elements are configured to electrically couple to an energy storage device that stores energy generated by the one or more thermoelectric elements when dissipating heat from the distal electrode.

5. The implantable medical device lead of claim 1, wherein the one or more thermoelectric elements are configured to electrically couple to a heat sink that dissipates energy generated by the one or more thermoelectric elements when dissipating heat from the distal electrode.

6. The implantable medical device lead of claim 1, wherein the one or more thermoelectric elements are arranged circumferentially around a distal end of the implantable medical device lead.

7. The implantable medical device lead of claim 1, wherein the one or more thermoelectric elements are arranged at a distal tip of the implantable medical device lead, and wherein the one or more thermoelectric elements include a central metal element and a metal ring element separated by a ring of heat transfer junction material.

8. A medical device comprising:
a pulse generator including an energy storage device; and
a lead including a lead body, an outer conductive coil extending through the lead body, and an inner conductive coil extending coaxially with the outer conductive coil, the outer conductive coil coupled to a proximal electrode at a distal end of the outer conductive coil, and the inner conductive coil coupled to a distal electrode at a distal end of the inner conductive coil;
a cooling assembly thermally coupled to the distal electrode and electrically coupled to the pulse generator to dissipate heat generated at the distal electrode during exposure to magnetic resonance imaging (MRI) fields, wherein the cooling assembly comprises one or more thermoelectric elements encased in a thermally conductive biocompatible material, and wherein the one or more thermoelectric elements are electrically coupled to the energy storage device to store energy generated by the one or more thermoelectric elements when dissipating heat from the distal electrode.

9. The medical device of claim 8, wherein the pulse generator includes an energy storage device, and wherein the one or more thermoelectric elements are electrically coupled to the energy storage device, the energy storage device driving the one or more thermoelectric elements to pull heat from the distal electrode.

10. The medical device of claim 9, wherein energy generated during exposure of the implantable medical device lead to MRI fields is stored in the energy storage device, and wherein the one or more thermoelectric elements are driven at least in part by the energy stored in the energy storage device during exposure of the implantable medical device lead to MRI fields.

11. The medical device of claim 8, wherein the pulse generator includes a heat sink, and wherein the one or more thermoelectric elements are electrically coupled to the heat sink to dissipate energy generated by the one or more thermoelectric elements when dissipating heat from the distal electrode.

12. The medical device of claim 8, wherein the one or more thermoelectric elements are arranged circumferentially around a distal end of the implantable medical device lead.

13. The medical device of claim 8, wherein the one or more thermoelectric elements are arranged at a distal tip of the implantable medical device lead, and wherein the one or more thermoelectric elements include a central metal element and a metal ring element separated by a ring of heat transfer junction material.

14. A medical device comprising:
a pulse generator including an energy storage device; and
a lead comprising:
an insulative lead body;
a conductor assembly extending through the lead body and including at least first, second, and third filars, wherein the first filar is coupled to the pulse generator at a proximal end of the first filar and to a distal electrode at a distal end of the first filar; and
a cooling assembly thermally coupled to the distal electrode to dissipate heat generated at the distal electrode during exposure to magnetic resonance imaging (MRI) fields, the cooling assembly electrically coupled to the energy storage device via the second and third filars, wherein the energy storage device drives the cooling assembly to pull heat from the distal electrode, wherein the cooling assembly comprises one or more thermoelectric elements encased in a thermally conductive biocompatible material, wherein the cooling assembly generates energy when dissipating heat from the distal electrode, and wherein the energy generated by the cooling assembly is stored in the energy storage device.

15. The medical device of claim 14, wherein the first, second, and third filars of the conductor assembly are co-radial.

16. The medical device of claim 14, wherein the one or more thermoelectric elements are arranged circumferentially around a distal end of the implantable medical device lead.

17. The medical device of claim 14, wherein the one or more thermoelectric elements are arranged at a distal tip of the implantable medical device lead, and wherein the one or more thermoelectric elements include a central metal element and a second metal ring element separated by a ring of heat transfer junction material.

* * * * *